United States Patent [19]

Allison et al.

[11] 4,117,113

[45] Sep. 26, 1978

[54] IMMUNOLOGICAL PREPARATIONS

[75] Inventors: Anthony Clifford Allison, Mill Hill; Gregory Gregoriadis, Kenton, both of England

[73] Assignee: National Research Development Corporation, London, England

[21] Appl. No.: 826,409

[22] Filed: Aug. 22, 1977

Related U.S. Application Data

[63] Continuation-in-part of Ser. No. 590,270, Jun. 25, 1975, Pat. No. 4,053,585.

[30] Foreign Application Priority Data

Jun. 25, 1974 [GB] United Kingdom ............... 28131/74

[51] Int. Cl.$^2$ ...................... A61K 39/12; A61K 39/18
[52] U.S. Cl. ...................................... 424/89
[58] Field of Search .................................... 424/88, 89

[56] References Cited

U.S. PATENT DOCUMENTS 4,053,585  10/1977  Allison et al. ................. 424/92

FOREIGN PATENT DOCUMENTS 2,249,552  5/1973  Fed. Rep. of Germany.
2,532,317  1/1976  Fed. Rep. of Germany.
7,301,850  11/1973  South Africa.

OTHER PUBLICATIONS

Haywood, A. M. J. Mol. Biol., 1974 83(4): 427–436 "Characteristics of Sendai Virus Receptors in a Model Membrane".
Haywood, A. M. J. Mol. Biol. 1974 87(3): 625–628 "Fusion of Sendai Viruses with Model Membranes".
Gregoriadis, G. et al., F.E.B.S. Letters 1974 45(1): 71–74 "Entrapment of Proteins in Liposomes Prevents Allergic Reactions in Preimmunized Mice".
Mooney, J. J. et al., J. Virol. 1975 15(2): 225–231 "Interaction of Sindbis Virus with Liposomal Model Membranes".
Heath, T. D. et al., Biochem. Soc. Trans. 1976 4(1): 129–133 "The Adjuvant Properties of Liposomes".
Wilson, T. et al., Proc. Natl. Acad. Sci. U.S.A. 74(8): 3471–3475 "Biological Properties of Poliovirus Encapsulated in Lipid Vesicles" (1977).

Primary Examiner—Shep K. Rose
Attorney, Agent, or Firm—Jacobs & Jacobs

[57] ABSTRACT

Immunological preparations are described in which liposomes having negative charge are used as adjuvants for the purposes of human and veterinary vaccines containing viral antigens. The formulation of influenza antigen in liposomes formed with egg lecithin is described and the adjuvant effect demonstrated.

14 Claims, No Drawings

IMMUNOLOGICAL PREPARATIONS

The present application is a continuation-in-part derived from our co-pending application Ser. No. 590,270, filed June 25, 1975, now U.S. Pat. No. 4,053,585.

This invention relates to immunological preparations including antigen compositions, for example viral vaccines, and is more particularly concerned with immunological preparations containing adjuvants.

Adjuvants are substances that enhance the immune response of a specific antigen. Examples of adjuvants are Freund's incomplete adjuvant, a water-in-oil emulsion containing the antigen, and Freund's complete adjuvant, which is the same with killed tubercle bacilli. Unfortunately, the mineral oils currently available for use as adjuvants are not readily degraded in man and persist at the injection site thereby causing unacceptable granulomas or other undesirable effects. This is however a real need for a safe and effective adjuvant for use in human immunization programmes. Such an adjuvant could reduce the amounts of antigens required for protective immunization, with corresponding economies especially relevant to the developing countries. The need for improved adjuvants in veterinary vaccines also exists.

Furthermore, it is desirable to administer as many vaccines as possible at the same time, so that one or a few injections can immunize humans or animals against a wide range of organisms or their toxic products. This is especially relevant to tropical countries where, in addition to the infections of temperate climates, there is exposure to many parasitic infections. When two or more antigens are administered simultaneously, each may reduce the formation of antibodies against the other by a phenomenon known as antigenic competition. In addition, the choice of suitable adjuvant materials is also controlled by the need to avoid allergic reactions.

It has now been found that preparations based on lipids when in the form of "liposomes" (which term will be defined hereinafter) are excellent in many respects as adjuvants provided the surface of the liposome carries a negative charge. Adjuvant preparations based on negatively charged liposomes elicit the formation of much higher concentrations of antibodies than are elicited by the use of free antigen. On the other hand, antigens entrapped in positively charged liposomes elicit less antibody than the same dose of the free antigen. Although liposomes have been proposed in a number of publications for the entrapment of drugs and other substances, their previous use in the formation of immunologically effective preparations has not been proposed. Indeed, the mechanism by which liposomes containing other active materials are believed to act in vivo would be considered contra-indicative of their use in connection with antigenic and like materials.

According to the present invention a pharmaceutical preparation for administration in vivo to effect immunization comprises an immunologically effective agent selected from viral antigens which agent is incorporated essentially entrapped in liposomes, said liposomes having a negative charge.

Liposomes have been described in the literature and their general structure is well known to biological research workers. Liposomes are onion-like structures comprising a series of lipid layers spaced one from another by aqueous material, the outermost layer being lipid. A broad variety of lipid materials may be used to form liposomes. Preferred lipids are those which are non-immunogenic and bio-degradable, notably the phospholipids such as natural lecithins, for example egg lecithin, or synthetic lecithins, for example dipalmitoyl lecithin. Such materials fulfull the requirements indicated above and possess certain additional advantages. Since the active material is entrapped within the liposome structure, higher doses can be given than with the free antigen. Furthermore, the immunological agent is retained within the liposome structure until it reaches the site of action and therefore allergic reactions are considerably reduced.

Liposomes also facilitate the use of multiple antigens including those which should be maintained out of contact with one another at least for a time. Competitive antigens can be incorporated in different populations of liposomes carrying different components, and mixtures of these can be administered together. The adjuvant effect of compositions in accordance with the invention may be further enhanced by incorporating other materials which hav adjuvant activity into the liposomes, for example saponins.

Liposomes are versatile carriers for antigens, adjuvants or other biologically active compounds. They have both aqueous and lipid compartments, and substances of very high molecular weight can be incorporated into them. Compounds of molecular weight up to about 300,000 daltons can be entrapped in smaller liposomes and the larger multilamellar liposomes can be used for molecular weights of 500,000 and above. The chemical composition of the liposomes, and with it properties such as charge, can be varied over a wide range, and materials can be attached to the surface of liposomes as well as incorporated within them. As indicated above, the adjuvant effect is achieved only with liposomes which are negatively charged. A suitably charged liposome surface can be achieved in the course of preparing the liposome, for example, with the use of added acidic substances.

In the preparation of preferred liposome structures in accordance with the invention it is customary to use a phospholipid such as egg lecithin as the main liposome-former. In addition, other lipids, for example cholesterol, may be used in somewhat smaller proportions as a membrane strengthener. A third component will be the substance which is responsible for the negatively charged liposome surface, for example phosphatidic acid, dicetyl phosphate or beef brain ganglioside. The components may be present in the ratio, for example, of lecithin (7 moles), cholesterol (2 moles) and phosphatidic acid or equivalent (1 mole). Other substances may be incorporated into the structure for various purposes.

The invention will now be further described by means of specific Examples:

EXAMPLE 1

Egg lecithin (30mg), cholesterol (4.4mg) and dicetyl phosphate (DP) (3.1mg) are dissolved in chloroform (3-4 ml) in a 50 ml spherical flask and evaporated under vacuum at 37° C. The thin lipid layer on the walls of the flask is then dispersed with detergent-extracted A/Port Chalmers (Evans Medical) influenza virus haemagglutinin (2,080 International units) and neuraminidase (2,000 International units) (IVHN). The suspension is allowed to stand at room temperature for about 2 hours during which time liposomes form and mature. The suspension is then sonicated for 10 seconds at 4° C in a MSE sonicator using a ¾ inch probe and maximum agitation. Several hours later the suspension is passed through a Sepharose 6B column to separate the influenza virus antigen incorporating liposomes.

The adjuvant effect of liposome entrapment of the influenza virus antigens on the immune response of guinea pigs to these antigens is tested as follows. Each guinea pig in two groups of five guinea pigs is inoculated intramuscularly with A/Port Chalmers influenza virus haemagglutinin (104 International units) and neuraminidase (100 International units), one group with the antigens in the free form and the other with the liposome entrapped antigens. The guinea pigs are bled after 20 days and on the same day are re-inoculated with the same dose of viral antigens, and bled again after a further 12 days. The sera are assayed by radial diffusion and the primary and secondary responses determined. Results typical of those obtained are shown in Table 1, the various antibody responses being expressed in units of $mm^2$.

Table 1

The Immune Responses Produced by Various Formulations of Influenza Virus Haemagglutinin and Neuraminidase

| Preparation | Primary response | Secondary response |
| --- | --- | --- |
| Free IHVN | 0 | 9.7 |
| IHVN incorporated in negative liposomes (DP) | 0 | 13.5 |

EXAMPLE 2

Liposomes entrapped solubilized A/Port Chalmers (Evans Medical) influenza haemagglutinin and neuraminidase (IVHN) is prepared essentially by the method of Example 1 but using phosphatidic acid (PA) in place of dicetyl phosphate (molar ratios of egg lecithin:cholesterol:phosphatidic acid are 7:1:1). A further liposome preparation is made which also incorporates as an additional adjuvant a water-soluble derivative of mycobacterial cell walls (FEBS Letters, 1973, 35, 317).

The adjuvant effect of liposome entrapment of the influenza virus antigens on the immune response of guinea pigs to these antigens is tested as follows. One of five treatments is administered intramuscularly to each guinea pig of a group of five guinea pigs, these treatments being: (A) IVHN alone; (B) IVHN incorporated in negatively charged liposomes (PA); (C) IVHN + derivative of mycobacterial cell walls; (D) IHVN + derivative of mycobacterial cell walls incorporated in negative liposomes (PA); and (E) IVHN + alum. The guinea pigs are bled for measurement of primary responses after 21 days, and on the same day they receive a repeat intramuscular injection of IVHN in the same form as previously. The guinea pigs are bled for measurement of secondary responses after a further 14 days. Antibody responses against haemagglutinin are measured by the single radial diffusion technique of Schild. Results typical of those obtained are shown in Table 2, the various antibody responses being expressed in units of $mm^2$.

These results show that the solubilized influenza virus envelope antigens are more immunogenic when incorporated with liposomes than when administered free. Incorporation with the liposomes of the water-soluble derivative of mycobacterial cell walls increases the antibody responses further so that these responses are significantly greater than those obtained with the conventional alum-associated antigens. Moreover the liposome incorporated antigen is completely degraded and does not elicit any residual inflammatory response at the site of administration.

Table 2

The Immune Responses Produced by Various Formulations of Influenza Virus Haemagglutinin and Neuraminidase

| Preparation | Primary responses | Secondary responses |
| --- | --- | --- |
| A. IHVN alone | 0 | 8.8 |
| B. IHVN incorporated in negative liposomes (PA) | 1.1 | 13.7 |
| C. IHVN + drivative of mycobacerial cell walls | 2.3 | 24.1 |
| D. IHVN + derivative of mycobacterial cell walls incorporated in negative liposomes (PA) | 0.6 | 11.6 |
| E. IHVN + alum | 0.6 | 12.1 |

Statistical analysis (Mann-Whitney)

| | |
| --- | --- |
| Primary responses | C>B, D, E $p<0.05$ |
| Secondary responses | C>B, D, E $p<0.01$ |
| | A<B, D, E $p<0.05$ |

We claim:

1. A pharmaceutical preparation for administration in vivo to effect immunization comprising an immunologically effective agent selected from viral antigens which agent is incorporated essentially entrapped in liposomes, said liposomes having a negative charge.

2. A pharmaceutical preparation according to claim 1, formulated as dosage units for use in humans.

3. A pharmaceutical preparation according to claim 1, wherein the virus is an influenza virus.

4. A pharmaceutical preparation according to claim 1, wherein the liposomes are formed with egg lecithin.

5. A pharmaceutical preparation according to claim 1, in which the negative charge is due to the presence of a substance selected from phosphatidic acid, dicetyl phosphate and beef brain ganglioside.

6. A method for the immunization of humans and animals against viral infections which comprises administering to such humans and animals an immunologically effective agent selected from viral antigens which agent is incorporated essentially entrapped in liposomes, said liposomes having a negative charge.

7. A method according to claim 6, which comprises administering said immunologically effective agent to a human in unit dosage form.

8. A method according to claim 7, wherein the virus is an influenza virus.

9. A method according to claim 6, wherein the immunologically effective agent is administered by injection.

10. A pharmaceutical method which comprises mixing a viral antigen with a lipid, water and a substance capable of imparting a negative charge, sonicating this mixture to produce liposomes having a negative charge with which said viral antigen is incorporated essentially entrapped, and administering said liposomes to a human or animal to effect immunization thereof.

11. A method according to claim 10, wherein the lipid is egg lecithin.

12. A method according to claim 10, wherein the substance capable of imparting a negative charge is selected from phosphatidic acid, dicetyl phosphate and beef brain ganglioside.

13. In the art of parenterally administering viral antigens to patients susceptible to immunization therewith, the improvement which comprise administering such antigens essentially entrapped in negatively charged liposomes to enhance the immune response thereto.

14. The improvement of claim 13, wherein the viral antigen administered is an influenza virus antigen.

* * * * *